US010314947B2

(12) United States Patent
Speck et al.

(10) Patent No.: US 10,314,947 B2
(45) Date of Patent: *Jun. 11, 2019

(54) COATING FORMULATIONS FOR SCORING OR CUTTING BALLOON CATHETERS

(71) Applicant: Angioscore, Inc., Colorado Springs, CO (US)

(72) Inventors: Ulrich Speck, Berlin (DE); Madeleine Caroline Berg, Berlin (DE)

(73) Assignee: Angioscore, Inc., Colorado Springs, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/664,941

(22) Filed: Jul. 31, 2017

(65) Prior Publication Data

US 2017/0340778 A1    Nov. 30, 2017

Related U.S. Application Data

(63) Continuation of application No. 14/877,284, filed on Oct. 7, 2015, now Pat. No. 9,770,536, which is a continuation of application No. 13/628,627, filed on Sep. 27, 2012, now Pat. No. 9,173,977, which is a continuation of application No. PCT/EP2011/056179, filed on Apr. 18, 2011.

(30) Foreign Application Priority Data

Apr. 19, 2010   (EP) ..................... 10160347

(51) Int. Cl.
| | | |
|---|---|---|
| A61F 2/00 | (2006.01) | |
| A61L 29/08 | (2006.01) | |
| A61L 29/16 | (2006.01) | |
| A61L 31/16 | (2006.01) | |
| A61M 25/10 | (2013.01) | |
| A61B 17/3207 | (2006.01) | |
| A61L 29/14 | (2006.01) | |

(52) U.S. Cl.
CPC ...... *A61L 29/08* (2013.01); *A61B 17/320725* (2013.01); *A61L 29/143* (2013.01); *A61L 29/16* (2013.01); *A61L 31/16* (2013.01); *A61M 25/10* (2013.01); *A61M 25/104* (2013.01); *A61B 2017/320733* (2013.01); *A61L 2300/216* (2013.01); *A61L 2300/416* (2013.01); *A61L 2300/606* (2013.01); *A61L 2300/802* (2013.01); *A61M 2025/105* (2013.01); *A61M 2025/109* (2013.01)

(58) Field of Classification Search
CPC combination set(s) only.
See application file for complete search history.

(56) References Cited

U.S. PATENT DOCUMENTS

| | | |
|---|---|---|
| 2,701,559 A | 2/1955 | Cooper |
| 2,854,983 A | 10/1958 | Baskin |
| 3,045,677 A | 7/1962 | Wallace |
| 3,467,101 A | 9/1969 | Fogarty et al. |
| 3,825,013 A | 7/1974 | Craven |
| 4,327,736 A | 5/1982 | Inoue |
| 4,456,011 A | 6/1984 | Warnecke |
| 4,483,340 A | 11/1984 | Fogarty et al. |
| 4,578,061 A | 3/1986 | Lemelson |
| 4,604,762 A | 8/1986 | Robinson |
| 4,637,396 A | 1/1987 | Cook |
| 4,649,922 A | 3/1987 | Wiktor |
| 4,723,549 A | 2/1988 | Wholey et al. |
| 4,796,629 A | 1/1989 | Grayzel |
| 4,838,853 A | 6/1989 | Parisi |
| 4,887,613 A | 12/1989 | Farr et al. |
| 4,895,166 A | 1/1990 | Farr et al. |
| 4,921,484 A | 5/1990 | Hillstead |
| 4,942,788 A | 7/1990 | Farr et al. |
| 4,950,277 A | 8/1990 | Farr |
| 4,956,830 A | 9/1990 | Mock et al. |
| 4,966,604 A | 10/1990 | Reiss |
| 4,969,458 A | 11/1990 | Wiktor |
| 4,976,711 A | 12/1990 | Parins et al. |
| 4,986,807 A | 1/1991 | Farr |
| 4,986,830 A | 1/1991 | Owens et al. |
| 4,998,539 A | 3/1991 | Delsanti |
| 5,003,918 A | 4/1991 | Olson et al. |
| 5,019,088 A | 5/1991 | Farr |
| 5,019,089 A | 5/1991 | Farr |
| 5,026,384 A | 6/1991 | Farr et al. |
| 5,062,384 A | 11/1991 | Foley et al. |
| 5,062,648 A | 11/1991 | Gomringer |
| 5,071,407 A | 12/1991 | Termin et al. |
| 5,098,440 A | 3/1992 | Hillstead |
| 5,100,386 A | 3/1992 | Inoue |
| 5,100,423 A | 3/1992 | Fearnot |
| 5,101,682 A | 4/1992 | Radisch et al. |
| 5,102,402 A | 4/1992 | Dror et al. |
| 5,102,417 A | 4/1992 | Palmaz |
| 5,108,416 A | 4/1992 | Ryan et al. |
| 5,112,345 A | 5/1992 | Farr |

(Continued)

FOREIGN PATENT DOCUMENTS

| | | |
|---|---|---|
| CN | 1688350 A | 10/2005 |
| CN | 104689377 A | 6/2015 |

(Continued)

OTHER PUBLICATIONS

Cremers et al. Comparison of Two Different Paclitaxel-Coated Balloon Catheters in the Porcine Coronary Restenosis Model; Clin Res Cardiol (2009) 98:325-350; DOI 10.1007/s00392-009-0008-2.

(Continued)

*Primary Examiner* — Hasan S Ahmed

(57) ABSTRACT

The present invention is related to scoring or cutting balloon catheters carrying at least on a portion of their surface at least one drug or drug preparation and at least one lipophilic antioxidant at a ratio of 3-100% by weight of the at least one lipophilic antioxidant in relation to 100% by weight of the drug, wherein a combination of the at least one drug being a limus drug and the at least one lipophilic antioxidant being butylated hydroxytoluene is excluded.

19 Claims, No Drawings

(56) References Cited

U.S. PATENT DOCUMENTS

| | | |
|---|---|---|
| 5,116,318 A | 5/1992 | Hillstead |
| 5,120,322 A | 6/1992 | Davis et al. |
| 5,133,732 A | 7/1992 | Wiktor |
| 5,176,693 A | 1/1993 | Pannek et al. |
| 5,181,911 A | 1/1993 | Shturman |
| 5,190,058 A | 3/1993 | Jones et al. |
| 5,192,291 A | 3/1993 | Pannek et al. |
| 5,196,024 A | 3/1993 | Barath |
| 5,199,951 A | 4/1993 | Spears |
| 5,209,727 A | 5/1993 | Radisch et al. |
| 5,221,261 A | 6/1993 | Termin et al. |
| 5,221,727 A | 6/1993 | Kumpf et al. |
| 5,222,971 A | 6/1993 | Willard et al. |
| 5,224,945 A | 7/1993 | Pannek et al. |
| 5,224,949 A | 7/1993 | Gomringer et al. |
| 5,226,887 A | 7/1993 | Farr et al. |
| 5,243,997 A | 9/1993 | Uflacker et al. |
| 5,263,963 A | 11/1993 | Garrison et al. |
| 5,295,493 A | 3/1994 | Radisch et al. |
| 5,295,959 A | 3/1994 | Gurbel et al. |
| 5,304,121 A | 4/1994 | Sahatjian |
| 5,306,250 A | 4/1994 | March et al. |
| 5,308,354 A | 5/1994 | Zacca et al. |
| 5,308,356 A | 5/1994 | Blackshear, Jr. et al. |
| 5,318,576 A | 6/1994 | Plassche et al. |
| 5,320,634 A | 6/1994 | Vigil et al. |
| 5,336,178 A | 8/1994 | Kaplan et al. |
| 5,336,234 A | 8/1994 | Vigil et al. |
| 5,344,401 A | 9/1994 | Radisch et al. |
| 5,344,419 A | 9/1994 | Spears |
| 5,350,101 A | 9/1994 | Godlewski |
| 5,354,279 A | 10/1994 | Hofling |
| 5,370,614 A | 12/1994 | Amundson et al. |
| 5,376,077 A | 12/1994 | Gomringer |
| 5,419,777 A | 5/1995 | Hofling |
| 5,423,745 A | 6/1995 | Todd et al. |
| 5,443,078 A | 8/1995 | Uflacker |
| 5,443,446 A | 8/1995 | Shturman |
| 5,443,496 A | 8/1995 | Schwartz et al. |
| 5,449,372 A | 9/1995 | Schmaltz et al. |
| 5,449,373 A | 9/1995 | Pinchasik et al. |
| 5,456,666 A | 10/1995 | Campbell et al. |
| 5,456,667 A | 10/1995 | Ham et al. |
| 5,458,568 A | 10/1995 | Racchini et al. |
| 5,460,607 A | 10/1995 | Miyata et al. |
| 5,470,314 A | 11/1995 | Walinsky |
| 5,501,694 A | 3/1996 | Ressemann et al. |
| 5,524,635 A | 6/1996 | Uflacker et al. |
| 5,527,282 A | 6/1996 | Segal |
| 5,536,178 A | 7/1996 | Novelli |
| 5,538,504 A | 7/1996 | Linden et al. |
| 5,545,132 A | 8/1996 | Fagan et al. |
| 5,556,405 A | 9/1996 | Lary |
| 5,556,408 A | 9/1996 | Farhat |
| 5,562,620 A | 10/1996 | Klein et al. |
| 5,569,195 A | 10/1996 | Saab |
| 5,571,086 A | 11/1996 | Kaplan et al. |
| 5,571,523 A | 11/1996 | Lee et al. |
| 5,607,442 A | 3/1997 | Fischell et al. |
| 5,609,574 A | 3/1997 | Kaplan et al. |
| 5,616,149 A | 4/1997 | Barath |
| 5,620,457 A | 4/1997 | Pinchasik et al. |
| 5,624,433 A | 4/1997 | Radisch et al. |
| 5,628,746 A | 5/1997 | Clayman |
| 5,628,755 A | 5/1997 | Heller et al. |
| 5,643,210 A | 7/1997 | Iacob |
| 5,649,941 A | 7/1997 | Lary |
| 5,681,281 A | 10/1997 | Vigil et al. |
| 5,690,642 A | 11/1997 | Osborne et al. |
| 5,695,469 A | 12/1997 | Segal |
| 5,697,944 A | 12/1997 | Lary |
| 5,697,971 A | 12/1997 | Fischell et al. |
| 5,702,410 A | 12/1997 | Klunder et al. |
| 5,707,385 A | 1/1998 | Williams |
| 5,713,863 A | 2/1998 | Vigil et al. |
| 5,713,913 A | 2/1998 | Lary et al. |
| 5,730,698 A | 3/1998 | Fischell et al. |
| 5,733,303 A | 3/1998 | Israel et al. |
| 5,735,816 A | 4/1998 | Lieber et al. |
| 5,742,019 A | 4/1998 | Radisch et al. |
| 5,746,716 A | 5/1998 | Vigil et al. |
| 5,746,968 A | 5/1998 | Radisch et al. |
| 5,755,708 A | 5/1998 | Segal |
| 5,755,778 A | 5/1998 | Kleshinski |
| 5,755,781 A | 5/1998 | Jayaraman |
| 5,766,201 A | 6/1998 | Ravenscroft et al. |
| 5,766,238 A | 6/1998 | Lau et al. |
| 5,772,681 A | 6/1998 | Leoni |
| 5,776,141 A | 7/1998 | Klein et al. |
| 5,776,181 A | 7/1998 | Lee et al. |
| 5,779,698 A | 7/1998 | Clayman et al. |
| 5,792,144 A | 8/1998 | Fischell et al. |
| 5,792,415 A | 8/1998 | Hijlkema |
| 5,797,935 A | 8/1998 | Barath |
| 5,800,450 A | 9/1998 | Lary et al. |
| 5,807,355 A | 9/1998 | Ramzipoor et al. |
| 5,810,767 A | 9/1998 | Klein |
| 5,814,061 A | 9/1998 | Osborne et al. |
| 5,827,321 A | 10/1998 | Roubin et al. |
| 5,863,284 A | 1/1999 | Klein |
| 5,868,708 A | 2/1999 | Hart et al. |
| 5,868,719 A | 2/1999 | Tsukernik |
| 5,868,779 A | 2/1999 | Ruiz |
| 5,868,783 A | 2/1999 | Tower |
| 5,869,284 A | 2/1999 | Cao et al. |
| 5,873,852 A | 2/1999 | Vigil et al. |
| 5,891,090 A | 4/1999 | Thornton |
| 5,893,840 A | 4/1999 | Hull et al. |
| 5,902,475 A | 5/1999 | Trozera et al. |
| 5,904,679 A | 5/1999 | Clayman |
| 5,904,698 A | 5/1999 | Thomas et al. |
| 5,906,639 A | 5/1999 | Rudnick et al. |
| 5,916,166 A | 6/1999 | Reiss et al. |
| 5,919,200 A | 7/1999 | Stambaugh et al. |
| 5,954,742 A | 9/1999 | Osypka |
| 5,961,490 A | 10/1999 | Adams |
| 5,967,984 A | 10/1999 | Chu et al. |
| 5,980,486 A | 11/1999 | Enger |
| 5,987,661 A | 11/1999 | Peterson |
| 5,994,667 A | 11/1999 | Merdan et al. |
| 6,004,295 A | 12/1999 | Langer et al. |
| 6,013,055 A | 1/2000 | Bampos et al. |
| 6,036,686 A | 3/2000 | Griswold |
| 6,036,689 A | 3/2000 | Tu et al. |
| 6,036,708 A | 3/2000 | Sciver |
| 6,048,356 A | 4/2000 | Ravenscroft et al. |
| 6,053,913 A | 4/2000 | Tu et al. |
| 6,059,811 A | 5/2000 | Pinchasik et al. |
| 6,071,285 A | 6/2000 | Lashinski et al. |
| 6,071,286 A | 6/2000 | Mawad |
| 6,077,298 A | 6/2000 | Tu et al. |
| RE36,764 E | 7/2000 | Zacca et al. |
| 6,102,904 A | 8/2000 | Vigil et al. |
| 6,106,548 A | 8/2000 | Roubin et al. |
| 6,117,104 A | 9/2000 | Fitz |
| 6,117,153 A | 9/2000 | Lary et al. |
| 6,123,718 A | 9/2000 | Tu et al. |
| 6,129,706 A | 10/2000 | Janacek |
| 6,129,708 A | 10/2000 | Enger |
| 6,136,011 A | 10/2000 | Stambaugh |
| 6,146,323 A | 11/2000 | Fischell |
| 6,152,944 A | 11/2000 | Holman et al. |
| 6,156,254 A | 12/2000 | Andrews et al. |
| 6,156,265 A | 12/2000 | Sugimoto |
| 6,165,187 A | 12/2000 | Reger |
| 6,190,356 B1 | 2/2001 | Bersin |
| 6,190,403 B1 | 2/2001 | Fischell et al. |
| 6,193,686 B1 | 2/2001 | Estrada et al. |
| 6,197,013 B1 | 3/2001 | Reed et al. |
| 6,203,569 B1 | 3/2001 | Wijay |
| 6,206,910 B1 | 3/2001 | Berry et al. |
| 6,210,392 B1 | 4/2001 | Vigil et al. |
| 6,211,247 B1 | 4/2001 | Goodman |
| 6,224,625 B1 | 5/2001 | Jayaraman |

(56) References Cited

U.S. PATENT DOCUMENTS

| | | |
|---|---|---|
| 6,235,043 B1 | 5/2001 | Reiley et al. |
| 6,241,762 B1 | 6/2001 | Shanley |
| 6,245,040 B1 | 6/2001 | Inderbitzen et al. |
| 6,258,087 B1 | 7/2001 | Edwards et al. |
| 6,258,108 B1 | 7/2001 | Lary |
| 6,261,319 B1 | 7/2001 | Kveen et al. |
| 6,280,411 B1 | 8/2001 | Lennox |
| 6,283,947 B1 | 9/2001 | Mirzaee |
| 6,283,951 B1 | 9/2001 | Flaherty et al. |
| 6,287,336 B1 | 9/2001 | Globerman et al. |
| 6,289,568 B1 | 9/2001 | Miller et al. |
| 6,296,651 B1 | 10/2001 | Lary et al. |
| 6,299,604 B1 | 10/2001 | Ragheb et al. |
| 6,306,151 B1 | 10/2001 | Lary |
| 6,306,166 B1 | 10/2001 | Barry et al. |
| 6,309,414 B1 | 10/2001 | Rolando et al. |
| 6,312,459 B1 | 11/2001 | Huang et al. |
| 6,319,229 B1 | 11/2001 | Kim et al. |
| 6,319,230 B1 | 11/2001 | Palasis et al. |
| 6,319,242 B1 | 11/2001 | Patterson et al. |
| 6,319,251 B1 | 11/2001 | Tu et al. |
| 6,325,779 B1 | 12/2001 | Zedler |
| 6,325,813 B1 | 12/2001 | Hektner |
| 6,332,880 B1 | 12/2001 | Yang et al. |
| 6,355,013 B1 | 3/2002 | van Muiden |
| 6,355,059 B1 | 3/2002 | Richter et al. |
| 6,361,545 B1 | 3/2002 | Macoviak et al. |
| 6,364,856 B1 | 4/2002 | Ding et al. |
| 6,371,961 B1 | 4/2002 | Osborne et al. |
| 6,394,995 B1 | 5/2002 | Solar et al. |
| 6,415,009 B1 | 7/2002 | Toporov et al. |
| 6,416,494 B1 | 7/2002 | Wilkins |
| 6,416,539 B1 | 7/2002 | Hassdenteufel |
| 6,419,692 B1 | 7/2002 | Yang et al. |
| 6,425,882 B1 | 7/2002 | Vigil |
| 6,425,908 B2 | 7/2002 | Ravenscroft et al. |
| 6,440,158 B1 | 8/2002 | Saab |
| 6,447,501 B1 | 9/2002 | Solar et al. |
| 6,450,988 B1 | 9/2002 | Bradshaw |
| 6,450,989 B2 | 9/2002 | Dubrul et al. |
| 6,454,775 B1 | 9/2002 | Demarais et al. |
| 6,471,979 B2 | 10/2002 | New et al. |
| 6,475,233 B2 | 11/2002 | Trozera |
| 6,475,234 B1 | 11/2002 | Richter et al. |
| 6,475,236 B1 | 11/2002 | Roubin et al. |
| 6,478,807 B1 | 11/2002 | Foreman et al. |
| 6,500,186 B2 | 12/2002 | Lafontaine et al. |
| 6,515,099 B2 | 2/2003 | Sato et al. |
| 6,517,765 B1 | 2/2003 | Kelley |
| 6,540,722 B1 | 4/2003 | Boyle et al. |
| 6,551,310 B1 | 4/2003 | Ganz et al. |
| 6,554,795 B2 | 4/2003 | Bagaoisan et al. |
| 6,562,062 B2 | 5/2003 | Jenusaitis et al. |
| 6,565,528 B1 | 5/2003 | Mueller |
| 6,569,180 B1 | 5/2003 | Sirhan et al. |
| 6,575,993 B1 | 6/2003 | Yock |
| 6,592,548 B2 | 7/2003 | Jayaraman |
| 6,602,281 B1 | 8/2003 | Klein |
| 6,605,107 B1 | 8/2003 | Klein |
| 6,607,442 B2 | 8/2003 | Ogata et al. |
| 6,613,072 B2 | 9/2003 | Lau et al. |
| 6,616,650 B1 | 9/2003 | Rowe |
| 6,616,678 B2 | 9/2003 | Nishtala et al. |
| 6,626,861 B1 | 9/2003 | Hart et al. |
| 6,632,231 B2 | 10/2003 | Radisch et al. |
| 6,648,912 B2 | 11/2003 | Trout et al. |
| 6,652,548 B2 | 11/2003 | Evans et al. |
| 6,656,156 B2 | 12/2003 | Yang et al. |
| 6,656,351 B2 | 12/2003 | Boyle |
| 6,663,660 B2 | 12/2003 | Dusbabek et al. |
| 6,682,545 B1 | 1/2004 | Kester |
| 6,695,813 B1 | 2/2004 | Boyle et al. |
| 6,730,064 B2 | 5/2004 | Ragheb et al. |
| 6,743,196 B2 | 6/2004 | Barbut et al. |
| 6,746,463 B1 | 6/2004 | Schwartz |
| 6,783,542 B2 | 8/2004 | Eidenschink |
| 6,840,950 B2 | 1/2005 | Stanford et al. |
| 6,872,206 B2 | 3/2005 | Edwards et al. |
| 6,918,920 B1 | 7/2005 | Wang et al. |
| 6,939,320 B2 | 9/2005 | Lennox |
| 6,942,680 B2 | 9/2005 | Grayzel et al. |
| 6,951,566 B2 | 10/2005 | Lary |
| 7,011,654 B2 | 3/2006 | Dubrul et al. |
| 7,011,670 B2 | 3/2006 | Radisch et al. |
| 7,029,483 B2 | 4/2006 | Schwartz |
| 7,060,051 B2 | 6/2006 | Palasis |
| 7,108,684 B2 | 9/2006 | Farnan |
| 7,131,981 B2 | 11/2006 | Appling et al. |
| 7,172,609 B2 | 2/2007 | Radisch et al. |
| 7,186,237 B2 | 3/2007 | Meyer et al. |
| 7,232,432 B2 | 6/2007 | Fulton et al. |
| 7,303,572 B2 | 12/2007 | Melsheimer et al. |
| 7,354,445 B2 | 4/2008 | Nicholson et al. |
| 7,357,813 B2 | 4/2008 | Burgermeister |
| 7,396,358 B2 | 7/2008 | Appling et al. |
| 7,445,792 B2 | 11/2008 | Toner et al. |
| 7,445,795 B2 | 11/2008 | Bakhshaee et al. |
| 7,455,652 B2 | 11/2008 | Laird |
| 7,465,311 B2 | 12/2008 | Wang et al. |
| 7,494,497 B2 | 2/2009 | Weber |
| 7,517,352 B2 | 4/2009 | Evans et al. |
| 7,524,319 B2 | 4/2009 | Dubrul |
| 7,566,319 B2 | 7/2009 | McAuley et al. |
| 7,686,824 B2 | 3/2010 | Konstantino et al. |
| 7,691,119 B2 | 4/2010 | Farnan |
| 7,708,748 B2 | 5/2010 | Weisenburgh, II et al. |
| 7,708,753 B2 | 5/2010 | Hardert |
| 7,736,375 B2 | 6/2010 | Crow |
| 7,763,043 B2 | 7/2010 | Goodin et al. |
| 7,780,715 B2 | 8/2010 | Shaked et al. |
| 7,780,798 B2 | 8/2010 | Stinson et al. |
| 7,803,149 B2 | 9/2010 | Bates et al. |
| 7,811,622 B2 | 10/2010 | Bates et al. |
| 7,875,284 B2 | 1/2011 | Reyes et al. |
| 7,931,663 B2 | 4/2011 | Farnan et al. |
| 7,955,350 B2 | 6/2011 | Konstantino et al. |
| 7,963,942 B2 | 6/2011 | Chen |
| 7,976,557 B2 | 7/2011 | Kunis |
| 7,998,184 B2 | 8/2011 | Eidenschink |
| 8,043,259 B2 | 10/2011 | Radisch et al. |
| 8,052,703 B2 | 11/2011 | St. Martin et al. |
| 8,066,726 B2 | 11/2011 | Kelley |
| 8,080,026 B2 | 12/2011 | Konstantino et al. |
| 8,123,770 B2 | 2/2012 | Olsen et al. |
| 8,192,675 B2 | 6/2012 | Burton et al. |
| 8,221,444 B2 | 7/2012 | Wang et al. |
| 8,323,307 B2 | 12/2012 | Hardert |
| 8,348,987 B2 | 1/2013 | Eaton |
| 8,382,820 B2 | 2/2013 | Addonizio et al. |
| 8,454,637 B2 | 6/2013 | Aggerholm et al. |
| 8,574,248 B2 | 11/2013 | Kassab |
| 8,673,387 B2 | 3/2014 | Bates et al. |
| 8,685,050 B2 | 4/2014 | Schur et al. |
| 8,685,990 B2 | 4/2014 | Coats et al. |
| 9,011,896 B2 * | 4/2015 | Speck .................. A61L 29/16 424/423 |
| 9,072,812 B2 * | 7/2015 | Speck .................. A61L 29/16 |
| 9,078,951 B2 * | 7/2015 | Speck .................. A61L 29/16 |
| 9,101,684 B2 * | 8/2015 | Speck .................. A61L 29/16 |
| 9,173,977 B2 * | 11/2015 | Speck .................. A61L 29/16 |
| 9,629,942 B2 * | 4/2017 | Speck .................. A61L 29/16 |
| 9,770,536 B2 | 9/2017 | Speck et al. |
| 2001/0001113 A1 | 5/2001 | Lim et al. |
| 2001/0001823 A1 | 5/2001 | Ryan |
| 2001/0007082 A1 | 7/2001 | Dusbabek et al. |
| 2001/0012950 A1 | 8/2001 | Nishtala et al. |
| 2001/0016753 A1 | 8/2001 | Caprio et al. |
| 2002/0010487 A1 | 1/2002 | Evans et al. |
| 2002/0010489 A1 | 1/2002 | Grayzel et al. |
| 2002/0029015 A1 | 3/2002 | Camenzind et al. |
| 2002/0037358 A1 | 3/2002 | Barry et al. |
| 2002/0038144 A1 | 3/2002 | Trout et al. |
| 2002/0045930 A1 | 4/2002 | Burg et al. |
| 2002/0065548 A1 | 5/2002 | Birdsall et al. |

(56) References Cited

U.S. PATENT DOCUMENTS

| | | |
|---|---|---|
| 2002/0091438 A1 | 7/2002 | Trozera |
| 2002/0111633 A1 | 8/2002 | Stoltze et al. |
| 2002/0165599 A1 | 11/2002 | Nasralla |
| 2002/0193873 A1 | 12/2002 | Brucker et al. |
| 2003/0018376 A1 | 1/2003 | Solar et al. |
| 2003/0023200 A1 | 1/2003 | Barbut et al. |
| 2003/0028235 A1 | 2/2003 | McIntosh et al. |
| 2003/0032973 A1 | 2/2003 | Jenusaitis et al. |
| 2003/0065381 A1 | 4/2003 | Solar et al. |
| 2003/0074046 A1 | 4/2003 | Richter |
| 2003/0078606 A1 | 4/2003 | Lafontaine et al. |
| 2003/0097169 A1 | 5/2003 | Brucker et al. |
| 2003/0105509 A1 | 6/2003 | Jang et al. |
| 2003/0114915 A1 | 6/2003 | Mareiro et al. |
| 2003/0144683 A1 | 7/2003 | Sirhan et al. |
| 2003/0149468 A1 | 8/2003 | Wallsten |
| 2003/0152870 A1 | 8/2003 | Huang |
| 2003/0153870 A1 | 8/2003 | Meyer et al. |
| 2003/0171799 A1 | 9/2003 | Lee et al. |
| 2003/0187494 A1 | 10/2003 | Loaldi |
| 2003/0195609 A1 | 10/2003 | Berenstein et al. |
| 2003/0199970 A1 | 10/2003 | Shanley |
| 2003/0199988 A1 | 10/2003 | Devonec et al. |
| 2003/0208244 A1 | 11/2003 | Stein et al. |
| 2003/0208255 A1 | 11/2003 | O'Shaughnessy et al. |
| 2004/0034384 A1 | 2/2004 | Fukaya |
| 2004/0106975 A1 | 6/2004 | Solovay et al. |
| 2004/0111108 A1 | 6/2004 | Robert Faman |
| 2004/0127475 A1 | 7/2004 | New et al. |
| 2004/0133223 A1 | 7/2004 | Weber |
| 2004/0143287 A1 | 7/2004 | Konstantino et al. |
| 2004/0193257 A1 | 9/2004 | Wu et al. |
| 2004/0208985 A1 | 10/2004 | Rowan et al. |
| 2004/0210299 A1 | 10/2004 | Rogers et al. |
| 2004/0230293 A1 | 11/2004 | Yip et al. |
| 2004/0243158 A1 | 12/2004 | Konstantino et al. |
| 2005/0010278 A1 | 1/2005 | Vardi et al. |
| 2005/0021070 A1 | 1/2005 | Feld et al. |
| 2005/0021071 A1 | 1/2005 | Konstantino et al. |
| 2005/0033417 A1 | 2/2005 | Borges et al. |
| 2005/0037048 A1 | 2/2005 | Song |
| 2005/0070888 A1 | 3/2005 | DiMatteo et al. |
| 2005/0080478 A1 | 4/2005 | Barongan |
| 2005/0083768 A1 | 4/2005 | Hara |
| 2005/0119723 A1 | 6/2005 | Peacock |
| 2005/0131512 A1 | 6/2005 | Vonderwalde |
| 2005/0137690 A1 | 6/2005 | Salahieh et al. |
| 2005/0271844 A1 | 12/2005 | Mapes et al. |
| 2005/0278021 A1 | 12/2005 | Bates et al. |
| 2005/0288629 A1 | 12/2005 | Kunis |
| 2006/0004323 A1 | 1/2006 | Chang et al. |
| 2006/0015133 A1 | 1/2006 | Grayzel et al. |
| 2006/0020243 A1 | 1/2006 | Speck et al. |
| 2006/0074484 A1 | 4/2006 | Huber |
| 2006/0085025 A1 | 4/2006 | Farnan et al. |
| 2006/0111736 A1 | 5/2006 | Kelley |
| 2006/0112536 A1 | 6/2006 | Herweck et al. |
| 2006/0129093 A1 | 6/2006 | Jackson |
| 2006/0149308 A1 | 7/2006 | Melsheimer et al. |
| 2006/0173487 A1 | 8/2006 | Uflacker et al. |
| 2006/0184191 A1 | 8/2006 | O'Brien |
| 2006/0240014 A1 | 10/2006 | Sukhatme |
| 2006/0247674 A1 | 11/2006 | Roman |
| 2006/0259005 A1 | 11/2006 | Konstantino et al. |
| 2006/0259062 A1 | 11/2006 | Konstantino |
| 2006/0270193 A1 | 11/2006 | Hidaka et al. |
| 2007/0020380 A1 | 1/2007 | Ding |
| 2007/0037739 A1 | 2/2007 | Wang et al. |
| 2007/0112422 A1 | 5/2007 | Dehdashtian |
| 2007/0128242 A1 | 6/2007 | Zhao |
| 2007/0185513 A1 | 8/2007 | Woolfson et al. |
| 2007/0190103 A1 | 8/2007 | Hossainy et al. |
| 2007/0198047 A1 | 8/2007 | Schon et al. |
| 2007/0212394 A1 | 9/2007 | Reyes et al. |
| 2007/0213808 A1 | 9/2007 | Roubin et al. |
| 2008/0021385 A1 | 1/2008 | Barry et al. |
| 2008/0118544 A1 | 5/2008 | Wang |
| 2008/0181927 A1 | 7/2008 | Zhao |
| 2008/0241215 A1 | 10/2008 | Falotico et al. |
| 2008/0300610 A1 | 12/2008 | Chambers |
| 2009/0105686 A1 | 4/2009 | Snow et al. |
| 2009/0105687 A1 | 4/2009 | Deckman et al. |
| 2009/0136560 A1 | 5/2009 | Bates et al. |
| 2009/0246252 A1 | 10/2009 | Arps et al. |
| 2009/0246253 A1 | 10/2009 | Ding |
| 2009/0264859 A1 | 10/2009 | Mas |
| 2009/0281490 A1 | 11/2009 | McAuley et al. |
| 2009/0306582 A1 | 12/2009 | Granada et al. |
| 2010/0042121 A1 | 2/2010 | Schneider et al. |
| 2010/0121372 A1 | 5/2010 | Farnan |
| 2010/0179647 A1 | 7/2010 | Carpenter et al. |
| 2010/0209472 A1 | 8/2010 | Wang |
| 2010/0233228 A1 | 9/2010 | Speck |
| 2010/0233236 A1 | 9/2010 | Zhao |
| 2010/0278997 A1 | 11/2010 | Speck et al. |
| 2010/0285085 A1 | 11/2010 | Stankus et al. |
| 2010/0286720 A1 | 11/2010 | Shaked et al. |
| 2010/0286721 A1 | 11/2010 | Goodin et al. |
| 2010/0324645 A1 | 12/2010 | Stankus et al. |
| 2011/0054396 A1 | 3/2011 | Kangas et al. |
| 2011/0082483 A1 | 4/2011 | Diamant et al. |
| 2011/0125247 A1 | 5/2011 | Farnan et al. |
| 2011/0143014 A1 | 6/2011 | Stankus et al. |
| 2011/0160756 A1 | 6/2011 | Aggerholm et al. |
| 2011/0196340 A1 | 8/2011 | Barry et al. |
| 2011/0230818 A1 | 9/2011 | Kunis |
| 2011/0264039 A1 | 10/2011 | Thielen et al. |
| 2011/0270177 A1 | 11/2011 | Chambers et al. |
| 2011/0295200 A1 | 12/2011 | Speck et al. |
| 2012/0059401 A1 | 3/2012 | Konstantino et al. |
| 2012/0172787 A1 | 7/2012 | McClain et al. |
| 2012/0215251 A1 | 8/2012 | Burton et al. |
| 2012/0239001 A1 | 9/2012 | Barry et al. |
| 2012/0277626 A1 | 11/2012 | Burbank et al. |
| 2013/0023817 A1 | 1/2013 | Speck et al. |
| 2013/0037777 A1 | 2/2013 | Mikawa et al. |
| 2013/0041315 A1 | 2/2013 | Speck |
| 2013/0041391 A1 | 2/2013 | Spencer et al. |
| 2013/0041399 A1 | 2/2013 | Hardert |
| 2013/0046237 A1 | 2/2013 | Speck et al. |
| 2013/0060127 A1 | 3/2013 | Burton et al. |
| 2013/0066346 A1 | 3/2013 | Pigott |
| 2013/0096604 A1 | 4/2013 | Hanson et al. |
| 2013/0150874 A1 | 6/2013 | Kassab |
| 2013/0211381 A1 | 8/2013 | Feld |
| 2013/0218181 A1 | 8/2013 | Feld et al. |
| 2013/0231638 A1 | 9/2013 | Speck et al. |
| 2014/0058358 A1 | 2/2014 | Kassab |
| 2014/0066960 A1 | 3/2014 | Feld et al. |
| 2014/0128801 A1 | 5/2014 | Speck et al. |
| 2014/0257181 A1 | 9/2014 | Speck |
| 2015/0297797 A1 | 10/2015 | Speck et al. |

FOREIGN PATENT DOCUMENTS

| | | |
|---|---|---|
| EP | 0565796 B1 | 5/1997 |
| EP | 0623315 B1 | 6/1999 |
| EP | 1169970 A1 | 1/2002 |
| EP | 1179323 A2 | 2/2002 |
| EP | 0832608 B1 | 3/2003 |
| EP | 1042997 B1 | 3/2005 |
| EP | 1581298 B1 | 8/2006 |
| EP | 1414373 B1 | 5/2008 |
| EP | 1337198 B1 | 6/2009 |
| EP | 1748816 B1 | 7/2010 |
| EP | 2063924 B1 | 10/2010 |
| EP | 2283890 A1 | 2/2011 |
| EP | 1962696 B1 | 3/2012 |
| EP | 1737530 B1 | 3/2013 |
| EP | 2564890 A1 | 3/2013 |
| EP | 2886136 A1 | 6/2015 |
| EP | 2886137 A1 | 6/2015 |
| JP | 2002126086 A | 5/2002 |
| JP | 2002126086 A1 | 5/2002 |

(56) References Cited

FOREIGN PATENT DOCUMENTS

| | | |
|---|---|---|
| JP | 2004148013 A1 | 5/2004 |
| JP | 2008504059 A | 5/2005 |
| JP | 2005343897 A | 12/2005 |
| JP | 5745030 B2 | 6/2013 |
| WO | WO1991002494 A1 | 3/1991 |
| WO | 9217118 A1 | 10/1992 |
| WO | WO1993001753 A2 | 2/1993 |
| WO | WO1994010919 A1 | 5/1994 |
| WO | 1994023787 A1 | 10/1994 |
| WO | WO1994023787 A1 | 10/1994 |
| WO | WO1994024946 A1 | 11/1994 |
| WO | WO1995003083 A1 | 2/1995 |
| WO | WO1998005377 A1 | 2/1998 |
| WO | WO1998045506 A1 | 10/1998 |
| WO | 1999017680 A1 | 4/1999 |
| WO | 1999055253 A1 | 11/1999 |
| WO | 1999062430 A1 | 12/1999 |
| WO | 02083011 A1 | 10/2002 |
| WO | 2002076509 A2 | 10/2002 |
| WO | WO2002083011 A1 | 10/2002 |
| WO | WO2003026536 A1 | 4/2003 |
| WO | WO2003039628 A2 | 5/2003 |
| WO | WO2003041760 A2 | 5/2003 |
| WO | 2004022124 A1 | 3/2004 |
| WO | 2004028582 A1 | 4/2004 |
| WO | WO2004028610 A2 | 4/2004 |
| WO | WO2004060460 A2 | 7/2004 |
| WO | WO2004066852 A2 | 8/2004 |
| WO | 2004108130 A1 | 12/2004 |
| WO | WO2005025458 A1 | 3/2005 |
| WO | 2006007173 A1 | 1/2006 |
| WO | 2009018816 A2 | 2/2009 |
| WO | 2009066330 A1 | 5/2009 |
| WO | 2009155405 A1 | 12/2009 |
| WO | 2013177175 A8 | 11/2013 |

OTHER PUBLICATIONS

EP Examination Report dated Oct. 9, 2013 from corresponding EP Application No. 10775805.4, 6 pages.
European Search Opinion issued in EP Application No. 15154222, dated May 18, 2015, 5 pages.
European search report and search opinion dated May 4, 2010 for EP 06770116.9.
European search report and search opinion dated Dec. 28, 2009 for EP 05792875.6.
European Search Report issued in EP Application No. 15154222 dated May 18, 2015. 2 pages.
Extended European Search Report issued in EP Application No. 11827369.7, dated Apr. 7, 2014. 6 pages.
File History for U.S. Appl. No. 11/411,635, filed Apr. 26, 2006.
File History for U.S. Appl. No. 13/044,425, filed Mar. 9, 2011.
File History for U.S. Appl. No. 13/842,080, filed Mar. 15, 2013.
First Examination Report dated Feb. 5, 2014 from corresponding EP Application No. 05733012.8.
International search report and written opinion dated Feb. 27, 2007 for PCT/US2006/017872.
International search report and written opinion dated May 23, 2006 for PCT /2005/009571.
International search report and written opinion dated Jul. 26, 2007 for PCT/2005/028809.
International search report and written opinion dated Nov. 4, 2004 for PCT/2004/000177.
International Search Report and Written Opinion issued in PCT Application No. PCTEP2010066754 dated May 1, 2011, 11 pages.
International Search Report and Written Opinion issued in PCT/US2011/052392 dated Jan. 11, 2012, 7 pages.
International Search Report issued in PCT/US2002/035547 dated May 20, 2003 , 3 Pages.
International Search Report issued in PCT/US2004/027836 dated Dec. 30, 2004 , 1 Page.
Japanese office action dated Jul. 9, 2010 for JP 2007-505113. (in Japanese with English translation).
Notification of Office Action dated Aug. 14, 2014 from corresponding JP Application No. 2013-505347.
Notification of the First Office Action dated Jan. 16, 2014, from corresponding Chinese Application No. 201080066293.3.
Scheller et al. Paclitaxel Balloon Coating, A Novel Method for Prevention and Therapy of Restenosis; Circulation. 2004;110:810-814, Aug. 9, 2004.
Supplementary European Search Report dated Nov. 20, 2013 from corresponding EP Application No. 05733012.8.
Suzuki et al. Anti-Oxidants for Therapeutic Use: Why Are Only a Few Drugs in Clinical Use? Advanced Drug Delivery Reviews, vol. 61, 2009, pp. 287-289.

* cited by examiner

COATING FORMULATIONS FOR SCORING OR CUTTING BALLOON CATHETERS

CROSS REFERENCE TO RELATED APPLICATIONS

This application is a continuation of U.S. patent application Ser. No. 14/877,284, filed Oct. 7, 2015, and issued as U.S. Pat. No. 9,770,536, which is a continuation of U.S. patent application Ser. No. 13/628,627, filed Sep. 27, 2012, and issued as U.S. Pat. No. 9,173,977, which is a continuation of PCT Application No. PCT/EP2011/056179, filed Apr. 18, 2011, which claims the benefit of EP Application No. 10160347.0, filed Apr. 19, 2010, the full disclosures of each of which are incorporated herein by reference in their entirety.

BACKGROUND

1. Field of the Invention

The invention relates to the transfer of a drug loosely adhering to the surface of a scoring or cutting balloon catheter to a site inside the body, usually in a diseased blood vessel. The preferred application is local drug therapy during percutaneous transluminal angioplasty (PTA) or percutaneous transluminal coronary angioplasty (PTCA). The interventions are performed to restore blood flow in stenotic or occluded blood vessels, usually into arteries. A catheter is introduced in a major artery. At the distal end the catheter carries a cylindrical balloon in folded state with very small diameter and additional tools or structures which scratch or cut the luminal surface of the treated blood vessel or tissue. In the folded state the balloon can enter or pass the stenotic or occluded segment of e.g. a blood vessel. Once positioned in the narrowed segment, the balloon is inflated to enlarge the lumen of the blood vessel to its original diameter. Simultaneously, a drug may be transferred to the vessel wall to prevent early and late re-narrowing due to hyperproliferation of the injured vessel wall.

Medical devices may contain drugs either to improve the tolerance, efficacy or in vivo life-time of the device or the device serves as carrier for the drug. In any case the dosedensity (e g. mg drug/mg device or mg drug/mm$^2$ device surface), chemical stability, adherence, release rate, and total amount released are important and frequently critical features of the drug formulation. These properties are the more critical the more the requirements during production and application of the device vary or may even be contradictory. Drug-coated angioplasty catheters are typical examples: the drug coating must adhere firmly to tolerate mechanical stress during production including folding of balloons, crimping of stents, packaging, transportation to customers, and during final application, which involves the passage through a narrow hemostatic valve, an introductory sheath or guiding catheter and a variable distance through possibly tortuous and narrow blood vessels. When the balloon is inflated the drug should be released within a minute or less as rapidly and as completely as possible. The problem was demonstrated by Cremers et al. (Cremers B, Biedermann M, Mahnkopf D, Bohm M, Scheller B. Comparison of two different paclitaxel-coated balloon catheters in the porcine coronary restenosis model. Clin Res Cardiol 2009; 98:325-330) who retrieved as much as 50% of the dose from balloons after expansion for one minute in coronary arteries of pigs, whereas other catheters coated with the same drug and dose but in a different formulation released more than 95%. Almost perfect results (i.e., loss of only 10% of dose and residual drug on the balloon after expansion in an artery of about 10%) were achieved with a rigid prototype balloon (Scheller B, Speck U, Abramjuk C, Bernhardt U, Bohm M, Nickenig G. Paclitaxel balloon coating—a novel method for prevention and therapy of restenosis. Circulation 2004; 110: 810-814). The application of the same coating composition to more flexible modern balloon catheters resulted in problems, i.e., larger premature loss of the drug. The coating of scoring or cutting balloons with drugs in a reliable way with a dose which sufficient to be efficacious imposes additional problems because of the more complex structure of the device and the more complex production process.

2. Prior Art

Protection from premature drug release. Premature release of a drug from a balloon is a major problem which has been addressed by a variety of methods. Some of them are mechanical, e.g. the use of protection tubes, sleeves, envelops. Examples are U.S. Pat. Nos. 5,370,614, 6,306, 166, and 6,616,650 disclosing various protective sheaths which are retracted before the balloon is inflated, or U.S. Pat. No. 6,419,692 proposing a cover which bursts during balloon expansion. A different approach is taken in U.S. Pat. No. 5,893,840 disclosing structured balloon membranes with tiny cavities, WO 94/23787 with roughened balloon membranes to enhance the adherence of coating, or more recently U.S. Pat. No. 7,108,684 proposing a pouch which protects the drug-containing layer on the balloon and WO 2009/066330 disclosing methods placing the drug selectively under the folds of a folded balloon. Although efficacious these methods have the disadvantage of increasing the complexity and cost of production or make handling of the devices more difficult or add to the diameter of the devices (which must be kept as small as possible to facilitate passage through stenotic lesions). In some embodiments the protective membranes or perforated membranes interfere with the scoring components of the balloons or prevent a homogeneous transfer of the drug to the tissue or even put the patient at risk. None of these methods has been applied to scoring or cutting balloons and nothing is known about problems which will arise from the increasing complexity and mechanical problems arising from a disturbance of the protecting envelops by the scoring or cutting structures and vice-versa.

Other approaches use either physical or chemical methods to control the release of drugs from a balloon surface, e.g. U.S. Pat. No. 5,304,121 describes a hydrogel which releases the drug only after exposure to a triggering agent; U.S. Pat. No. 5,199,951 relies on thermal activation; according to U.S. Pat. No. 7,445,792 a lipophilic 'hydration inhibitor' protects water-soluble drugs from premature release; and according to U.S. Pat. No. 5,370,614 a viscous matrix protects the drug from premature release, however, the viscous matrix must be protected by a sheath during the passage to the stenotic vessel segment. None of the methods has been tested in practice and proven to fulfill the requirements for fast, reliable and complete drug transfer to the target tissue. None of the methods has been designed to be used with scoring or cutting balloons.

Numerous methods of sustained drug release are known and successfully used in practice but are not applicable to medical devices which are in contact with the target tissue for only a few seconds or minutes. Sustained drug release is usually achieved by embedding the drug in a polymer which restricts the diffusion rate to the surface and in this way controls the transfer into the adjacent tissue.

Therefore, a need remains for a method or formulation which protects the coating from premature losses during production, handling, and on the way to the lesion and still allows the immediate and complete release of the active ingredient at a location and point in time determined by the user. During the production process this problem is even more severe for scoring and cutting balloons because of the more complex structure of the product. Scoring and cutting balloons have merits in the treatment of certain lesions, e.g. if the conventional smooth balloons tend to dislocate during inflation or if a controlled and predetermined injury of the vessel wall is preferred to an uncontrolled dissection during balloon inflation. Nevertheless, the problem of renarrowing of the vessel lumen due to excessive neointimal proliferation as a reaction to the unavoidable injury during dilatation is the same as with conventional balloon catheters.

An advantageous way to control adherence and release of a drug from a medical device, e.g., an angioplasty balloon, is the selection of a suitable formulation and coating which do not require mechanical protection, or additional physical or chemical interaction with the coating except the usual operation of the device e.g. inflation of a folded balloon to induce the release of the drug. Although desirable and frequently tried, the conflicting objectives of perfect adherence during production and before use and immediate release at the site of action make it a difficult task. A large variety of patent applications vaguely disclose measures, compositions and devices to solve this problem for conventional balloon catheters either by the selection of drugs, the choice of specific coating processes or formulations containing various additives. Long lists of compounds have been copied from textbooks of chemistry, pharmacology, or pharmacy but even with extensive experimentation disclosures are not sufficiently clear to allow a person familiar with the subject and skilled in the art to come to a satisfactory solution without an inventive step. Examples of prior art are US 2008/0118544 reciting an excessive number of substances and substance classes or U.S. Pat. No. 7,445,795 which discloses the use of hydration inhibitors' not applicable to the preferred class of very lipophilic drugs which require 'hydration enhancers' as e.g. disclosed in WO 2004/028582. Although the hydrophilic additives (which may be regarded as 'hydration enhancer') work quite well on certain conventional balloon membranes (Scheller B, Speck U, Abramjuk C, Bernhardt U, Bohm M, Nickenig G. Paclitaxel balloon coating—a novel method for prevention and therapy of restenosis. Circulation 2004; 110: 810-814) the adherence to various modern conventional or scoring PTA or PTCA balloons is either too weak or too tight resulting in premature loss of a major proportion of the drug or incomplete release at the target site. None of the known compositions has been tried on scoring or cutting balloon catheters.

Prior Art: Antioxidants.

In theory, antioxidants address an almost universal feature of diseased tissue, namely the Reactive oxygen species', and should have widespread medical applications. In practice, only very few controlled clinical trials have shown beneficial effects of antioxidants (Suzuki K. Antioxidants for therapeutic use: Why are only a few drugs in clinical use?Advanced Drug Delivery Reviews 2009; 61:287-289). Antioxidants are mentioned as potentially useful drugs for the treatment of focal vascular disease such as stenosis, restenosis, atherosclerotic plaques, and vulnerable plaques in US 2009/0136560 with no additive, in U.S. Pat. No. 5,571,523 as agents inducing apoptosis in vascular smooth muscle cells, in WO 2004/022124 either as active drugs or as 'hydration inhibitors'. In US 2008/0241215 probucol, a drug approved for the treatment of hyperlipidemia, a known risk factor for atherosclerosis, is proposed as the active ingredient in stent coating, either alone or combined with rapamycin or another anti-restenotic agent in a slow-release formulation. None of the above-mentioned documents contains data encouraging the use as additives to a lipophilic drug to delay the release rate of the drug and no specific compositions are disclosed which address the above-mentioned problems of adhesion of a drug before the target lesion is reached and immediate release when required.

Small proportions of antioxidants are commonly used to protect drugs or nutrients from decomposition by oxygen or oxidation, an application which has also been proposed for drugs coated on implantable medical devices such as stents (US 2007/0020380, US 2009/0246253) or balloon catheters (US 2009/0246252, especially paragraph [105]). However, antioxidants are commonly used in proportions of less than 1% by weight in relation to 100% by weight of the drug. Normally it is intended to use as less antioxidant as possible, i.e., less than 0.1% by weight in relation to 100% by weight of the drug (Voigt R. Lehrbuch der pharmazeutischen Technologie. 5. Edition, Verlag Chemie, Weinheim—Deer-field Beach, Fla.—Basel, 1984).

Present Invention.

The problem underlying the present invention was the provision of a scoring or cutting balloon catheter with an improved adherence of the drug without negative effect on the release of the drug at the target site.

The problem was solved by a scoring or cutting balloon catheter according to claim 1. In other words, the problem was solved by a scoring or cutting balloon catheter carrying at least on a portion of its surface at least one drug or drug preparation and at least one lipophilic antioxidant at a ratio of 3-100% by weight of the at least one lipophilic antioxidant in relation to 100% by weight of the drug, wherein a combination of limus drugs with butylated hydroxytoluene as the lipophilic antioxidant is excluded. Preferred embodiments are disclosed in the dependant claims.

During testing of a large variety of coating methods, additives and drug combinations the surprising discovery was made that certain lipophilic antioxidants added to even more lipophilic and less water soluble drugs in a defined mass ratio significantly increase the adherence of the drug to scoring and cutting balloons during handling and on the way to the target lesion even if the target lesion is located far away from the site where the device first enters a blood-filled introductory sheath, guiding catheter or vessel containing rapidly flowing blood. This was also tested with scoring balloons. In spite of the additional mechanical stress (as compared to conventional balloons) imposed on the coating due the movement of the scoring wires surrounding the folded balloons the loss of the drug during the passage through a narrow hemostatic valve and a 3 curved guiding catheter was very low. Thus, at least one lipophilic antioxidant in an amount of 3-100% by weight is used as an adherence improver for drugs coated on a scoring or cutting balloon catheter. The wording "at least one lipophilic antioxidant" means that single antioxidants but also mixtures of different antioxidants are included.

Preferred examples of active drugs are inhibitors of cell proliferation, preferably taxanes such as paclitaxel, docetaxel and protaxel, immunosuppressants belonging to the class of substances binding to the mammalian target of ra-pamycin (mTOR), i.e., mTOR inhibitors such as sirolimus, everolimus, zotarolimus, biolimus and temsirolimus, most preferred is sirolimus, referred to as limus-drugs. Alternatively, specific inhibitors of neovascularization such as thalidomide, statins like atorvastatin, cerivastatin, fluvastatin or anti-inflammatory drugs like corticoids or even more preferred lipophilic derivatives of corticoids such as betamethasone diproprionate or dexamethasone-21-palmitate. Various drugs may be applied or combined if different pharmacological actions are required or efficacy or tolerance is to be improved. Thus, the wording "at least one drug or drug preparation" means that single drugs but also mixtures of different drugs are included. Preferred drugs are either lipophilic (partition coefficient between n-butanol and water >10, or display very poor water solubility (<1 mg/ml, 20° C.).

Preferred additives to the active drugs are lipophilic antioxidants, particularly preferred are antioxidants which are solid at temperatures up to 40° C. Preferred are butylated hydroxytoluene, butylated hydroxyanisole, nordihydroguaiaretic acid, propyl gallate and ascorbyl palmitate. Probucol is not a preferred additive. The combination of mTOR-binding limus-drugs with butylated hydroxytoluene is excluded as already mentioned above. This applies to combinations of the single drug with the single antioxidant as well as to combinations of butylated hydroxytoluene with mixtures consisting of different Limus drugs.

Lipophilic antioxidant means that the partition coefficient of the antioxidant between n-butanol and water is >1, more preferred >10 and even more preferred >100.

Preferably, the drug is more lipophilic than the antioxidant, i.e., the partition coefficient between n-butanol and water of the drug is higher than the partition coefficient between n-butanol and water of the antioxidant.

At the dose density used the chosen antioxidants do not display relevant therapeutic or prophylactic effects in respect of the disease which is treated by the coated medical device nor is the relative amount of the antioxidant chosen to protect the drug from oxidative decomposition. The dose density and the mass relation of the antioxidant to the drug are solely optimized in respect of adherence of the drug to and release from the medical device surface. The antioxidant dose on the medical device is too low to provide the desired pharmacological effect, i.e., it is ineffective on its own. The antioxidant on the medical device is not required to protect the active drug (e.g., the antiproliferative drug) from oxidative decomposition during production, sterilization and storage; at least it is not required at the dose or concentration applied according to this invention. 'Not required' means that the active drug is stable enough without the antioxidant or at an antioxidant dose or dose density or ratio to the active drug below the dose according to the present invention. 'Sufficient stability' means that less than 5% of the active drug is lost due to oxidative decomposition between the coating of the device and the use in patients one year after production if stored at ambient temperature (=drug or drug preparation stable against oxidative decomposition).

The dose of the antioxidant on the surface of a medical device may be defined in respect of the therapeutic drug. Preferred relationships (weight/weight) are 3-100% antioxidant of the weight of the drug. For example, if the dose density of the drug is 5 µg/mm$^2$ device surface, the amount of antioxidant is 0.15-5.0 µg/mm$^2$. Higher proportions of the antioxidant may be selected if either the drug is applied at a dose below 3 µg/mm$^2$ device surface or the adherence of the drug to the device surface is further improved. The antioxidant load of the device may reach 10 µg/mm$^2$. A higher load is possible. Other preferred ranges for the relationship of antioxidant to drug on a weight/weight basis are 5-100%, more preferred 10-100%, and even more preferred 20-100% in relation to 100% of the drug. The relationship may also be defined in respect of moles in a preferred embodiment the antioxidant is present from 10 mole % relative to the drug to 200 mole %. Higher amounts of the antioxidant may be useful; they are only excluded if they display on their own significant pharmacological prophylactic or therapeutic effects in respect of the disease to be treated application of the same coating composition to more flexible modern balloon catheters resulted in problems, i.e., larger premature loss of the drug. The coating of scoring or cutting balloons with drugs in a reliable way with a dose which is sufficient to be efficacious imposes additional problems because of the more complex structure of the device and the more complex production process.

If more than one drug is used the total weight of the drugs or the total moles of the drugs serve as basis for the calculation of the amount of the antioxidant. If more than one antioxidant is used the total weight of the antioxidants or the total moles of the antioxidants serve as basis for the calculation of the amount of the antioxidants.

Polymer-free coating compositions are preferred. It is a special advantage of the present compositions that they do not require the use of polymers to prevent premature release of the drug.

Usually, drugs and mixtures of drugs with additives are coated on medical devices as liquid formulations in volatile solvents. The choice of solvent is important for the distribution of the drug on the device, especially if the device is coated at an advanced stage of production. An advanced stage of production of a scoring or cutting balloon may include the scoring or cutting elements of the device, the structures required to fix these elements and an already folded balloon. The solvents further determine the structure of the coating in dry state and the adherence and release of the drug from the surface. Preferred organic solvents are acetone, tetrahydrofuran, and various alcohols such as methanol and ethanol. Usually, 1 to 30% (volume/volume) water is added. The drug or drugs and the antioxidant may be applied at the same time dissolved in the same solvent or mixture of solvents. Alternatively, they may be separately dissolved in the same or different solvents and sequentially applied. In a preferred embodiment, the scoring or cutting balloon catheter has been coated with at least one drug and at least one antioxidant both together or each separately dissolved in tetrahydrofuran or a mixture of solvents containing more than 25% (v/v) tetrahydrofuran. Another preferred embodiment is based on a scoring or cutting balloon catheter, which has been coated with at least one drug and at least one antioxidant both together or each separately dissolved in acetone or a mixture of solvents containing more than 25% (v/v) acetone. Coating with dry particles such as micro- or nanoparticles, crystals, capsules etc. or particles suspended in a liquid preparation is possible. Coating with particles may be facilitated by a roughened or sticky surface of the medical device.

A variety of coating procedures providing more or less uniform layers on medical devices are known from the literature and are disclosed in patent applications. These include simple dipping, spraying, and methods providing precise doses and homogeneous distributions (e.g., WO 2009/018816). Coating may be applied stepwise, either as multiple layers of the same composition or as layers with different compositions e.g. the drug first and the antioxidant second or in the opposite order. All these methods may be applied to the formulations of the current invention. Furthermore, coated medical devices may be dried under different conditions such as temperature, air flow, gas composition, and pressure at different stages of the production process. They may be stored in water-vapor-tight seals with a separately packed water absorbing-agent within the seal.

Subject of the current invention are scoring or cutting balloon catheters, e.g., catheters for angioplasty or coronary angioplasty. Preferred are scoring or cutting balloon catheters for short-lasting use during an interventional image guided therapy. Short lasting use means that the device is not implanted but eliminated from the body when the procedure is finished, usually within less than 10 minutes, but never later than a few, preferably 5, hours after the end of the procedure. Catheters may contain balloon membranes made from various polymers and copolymers, polyam-ides (nylon 12, pebax), polyethylenes, polyurethanes, various polyvinyls and the like. Independently of the type of material, the adherence and release properties of drugs are improved by the addition of lipophilic antioxidants. Furthermore, catheters comprise elements which are aimed at scoring or cutting the surfaces in direct contact with the inflated balloons, e.g. wires with various profiles, or protrusions of the balloon surface.

The scoring or cutting balloon catheter carries the at least one drug or drug preparation and the at least one lipophilic antioxidant at least on a portion of its surface which is aimed at coming into close contact with the tissue to be treated, e.g., the balloon at the distal portion of a catheter shaft. This means that at least 5%, preferably more than 50%, most preferably more than 90% of the surface is coated. The balloon of a scoring or cutting balloon catheter has a central cylindrical part and two opposite conical ends. If less than 100% of the balloon catheter's surface is coated, it is preferred that the cylindrical part is coated and that at least parts of or the complete conical ends remain uncoated.

Below, the invention is described by means of Examples.

EXAMPLE 1

Balloons for percutaneous transluminal coronary angioplasty type A (AngioSculpt 3.5-20 mm, AngioScore, Inc., Fremont Calif., USA were coated either with paclitaxel alone or combined with iopromide (iodinated contrast agent according to WO 02/076509) or different amounts of butylated hydroxy-toluene (BHT); solvent:acetone/ethanol/$H_2O$. Coated balloons were tested in respect of paclitaxel loss during the passage through a hemostatic valve, Medtronic Launcher JL 3.5 6F guiding catheter and one minute in stirred blood (37° C.). When admixed at sufficient concentration to the coating solution, BHT improved the adhesion of paclitaxel.

| Coating solution | Catheter labeling | Loss on the way to the lesion % of dose |
|---|---|---|
| No additive | 1 | 24 |
|  | 2 | 40 |
| Iopromide as an additive; | 3 | 49 |
| ca. 0.5 mg/mg paclitaxel | 4 | 34 |
| BHT 5%-0.05 mg BHT/mg | 5 | 15 |
| paclitaxel | 6 | 26 |
| BHT 24%-0.24 mg BHT/mg | 7 | 10 |
| paclitaxel | 8 | 6 |

EXAMPLE 2

Balloons for percutaneous transluminal coronary angioplasty type A were coated either with paclitaxel alone or combined with iopromide (iodinated contrast agent according to WO 02/076509), see example 2, or butylated hydroxytoluene (BHT) or nordihydroguaj arctic acid. Coated balloons were tested in respect of paclitaxel loss during the passage through a hemostatic valve, a Medtronic Launcher JL 3.5 6F guiding catheter and in stirred blood (37° C.) for one minute. When admixed at sufficient concentration to the coating solution, lipophilic antioxidants improve the adhesion of paclitaxel whereas the release during balloon inflation in a coronary artery (determined in separate experiments) was not impaired.

| Coating solution | Labeling | Loss on the way to the lesion % of dose | Residual paclitaxel on balloons % of dose |
|---|---|---|---|
| No additive acetone/ethanol/$H_2O$ | Control 1, 2 | 32 | no data |
| Iopromide as an additive ca. 0.5 mg/mg paclitaxel; acetone/ethanol/$H_2O$ | Control 3, 4 | 42 | ~10 |
| BHT 24% = 0.24 mg BHT/mg paclitaxel, acetone/ethanol/$H_2O$ | A | 15.3 ± 9.5 | 11 |
| BHT 24% = 0.24 mg BHT/mg paclitaxel; tetrahydrofuran/ethanol/$H_2O$ | B | 3.4 ± 4.8 | 13 |
| Nordihydroguaiaretic acid 35% = 0.35 mg/mg paclitaxel; acetone/ethanol/$H_2O$ | C | 4.2 ± 7.2 | no data |

What is claimed is:

1. A method for performing angioplasty, comprising:
   providing a balloon catheter, the balloon catheter comprising:
   a shaft having a proximal portion and a distal portion;
   an inflatable balloon coupled to the distal portion of the shaft;
   a nonimplantable scoring structure surrounding the balloon;
   a coating composition carried on at least a portion of a surface of the balloon catheter, the coating composition comprising at least one drug and at least one lipophilic antioxidant, the coating composition being 3-100% by weight of the at least one drug, wherein the at least one drug is selected from the group consisting of a Limus drug, a cell proliferation inhibitor, and an inhibitor of neovascularization, wherein the at least one lipophilic antioxidant is selected from the group consisting of butylated hydroxytoluene, butylated hydroxyanisole, nordihydroguaiaretic acid, ascorbyl palmitate, and propyl gallate, wherein a combination of a Limus drug with butylated hydroxytoluene as the lipophilic antioxidant is excluded;
   moving the inflatable balloon, nonimplantable scoring structure, and coating composition toward an angioplasty site, the at least one lipophilic antioxidant protecting the at least one drug from premature loss when moving toward the angioplasty site; and
   inflating the inflatable balloon to cause the scoring structure to score a luminal surface of a blood vessel at the angioplasty site and deliver the at least one drug to the angioplasty site.

2. The method according to claim 1, wherein the scoring structure comprises one or more wires, and inflating the inflatable balloon causes the one or more wires to score the luminal surface of the blood vessel.

3. The method according to claim 1, wherein the at least one drug comprises an oxidation-insensitive taxane selected from the group consisting of paclitaxel, protaxel and docetaxel.

4. The method according to claim 3, wherein the at least one lipophilic antioxidant is nordihydroguaiaretic acid.

5. The method according to claim 3, wherein the oxidation-insensitive taxane is oxidation-insensitive paclitaxel.

6. The method according to claim 5, wherein the at least one lipophilic antioxidant is nordihydroguaiaretic acid.

7. The method according to claim 1, wherein the at least one lipophilic antioxidant is nordihydroguaiaretic acid.

8. The method according to claim 1, wherein the at least one antioxidant load is up to 10 µg/mm2 of coated catheter surface.

9. The method according to claim 8, wherein the at least one lipophilic antioxidant is nordihydroguaiaretic acid.

10. The method according to claim 1, wherein the at least one lipophilic antioxidant is contained at a ratio of 5-100% by weight, in relation to 100% by weight of the at least one drug.

11. The method according to claim 10, wherein the at least one lipophilic antioxidant is nordihydroguaiaretic acid and the at least drug comprises oxidation-insensitive paclitaxel.

12. The method according to claim 1, wherein the at least one lipophilic antioxidant is contained at a ratio of 10-100% by weight, in relation to 100% by weight of the at least one drug.

13. The method according to claim 12, wherein the at least one lipophilic antioxidant is nordihydroguaiaretic acid and the at least drug comprises oxidation-insensitive paclitaxel.

14. The method according to claim 1, wherein the at least one lipophilic antioxidant is contained at a ratio of 20-100% by weight, in relation to 100% by weight of the at least one drug.

15. The method according to claim 14, wherein the at least one lipophilic antioxidant is nordihydroguaiaretic acid and the at least drug comprises oxidation-insensitive paclitaxel.

16. The method according to claim 1, wherein the at least one lipophilic antioxidant is contained at a ratio of 50-100% by weight, in relation to 100% by weight of the at least one drug.

17. The method according to claim 16, wherein the at least one lipophilic antioxidant is nordihydroguaiaretic acid and the at least drug comprises oxidation-insensitive paclitaxel.

18. The method according to claim 1, wherein the balloon catheter further comprises a coating composition including the therapeutically effective amount of at least one drug and an amount of at least one lipophilic antioxidant, wherein the coating composition is polymer-free.

19. The method according to claim 18, wherein the at least one lipophilic antioxidant is nordihydroguaiaretic acid and the at least drug comprises oxidation-insensitive paclitaxel.

* * * * *